(12) United States Patent
Hogendijk

(10) Patent No.: US 6,887,220 B2
(45) Date of Patent: May 3, 2005

(54) CATHETER HAVING A COMPLIANT MEMBER CONFIGURED TO REGULATE ASPIRATION RATES

(75) Inventor: Michael Hogendijk, Palo Alto, CA (US)

(73) Assignee: Gore Enterprise Holdings, Inc., Newark, DE (US)

( * ) Notice: Subject to any disclaimer, the term of this patent is extended or adjusted under 35 U.S.C. 154(b) by 129 days.

(21) Appl. No.: 10/243,525

(22) Filed: Sep. 12, 2002

(65) Prior Publication Data

US 2004/0054348 A1 Mar. 18, 2004

(51) Int. Cl.[7] .............................................. A61M 1/00
(52) U.S. Cl. .................. 604/119; 604/34; 604/245; 604/537
(58) Field of Search .............................. 604/19, 30, 31, 604/34, 35, 118, 119, 167.01, 167.03, 167.04, 173, 207, 236, 237, 245–247, 249, 264, 523, 524, 525, 526, 527, 537, 540–544, 6.16, 96.01, 97.01; 606/191–194, 107, 127, 159, 166

(56) References Cited

U.S. PATENT DOCUMENTS

| | | | | |
|---|---|---|---|---|
| 3,469,582 A | * | 9/1969 | Jackson | 604/119 |
| 3,717,174 A | * | 2/1973 | Dewall | 137/565.15 |
| 3,881,483 A | * | 5/1975 | Sausse | 604/6.14 |
| 4,596,563 A | * | 6/1986 | Pande | 604/264 |
| 5,106,367 A | * | 4/1992 | Ureche et al. | 604/30 |
| 5,520,651 A | * | 5/1996 | Sutcu et al. | 604/118 |

* cited by examiner

Primary Examiner—Nicholas D. Lucchesi
Assistant Examiner—Jennifer J Maynard
(74) Attorney, Agent, or Firm—Kevin J. Boland

(57) ABSTRACT

The present invention is directed to a catheter that is configured to self-regulate aspiration rates through a working lumen of the catheter. The catheter comprises a compliant member in communication with the working lumen that is configured to transition from an open position to a closed position when a predetermined aspiration threshold is exceeded. In the closed position, the compliant member is temporarily drawn inward to at least partially occlude flow through the working lumen, thereby mitigating the rate of aspiration imposed upon a patient's vessel. When the rate of aspiration is reduced below the threshold level, the compliant member returns to the open position.

30 Claims, 6 Drawing Sheets

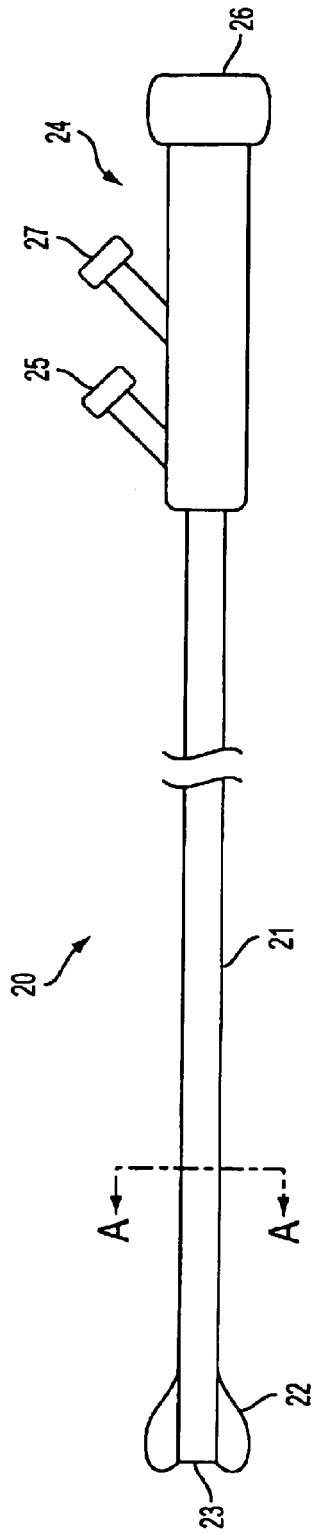
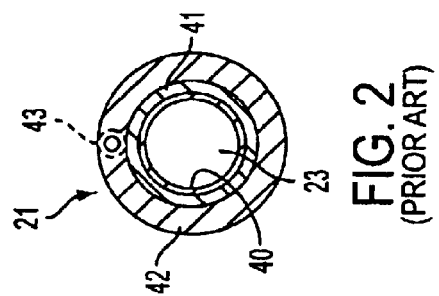
FIG. 1 (PRIOR ART)
FIG. 2 (PRIOR ART)

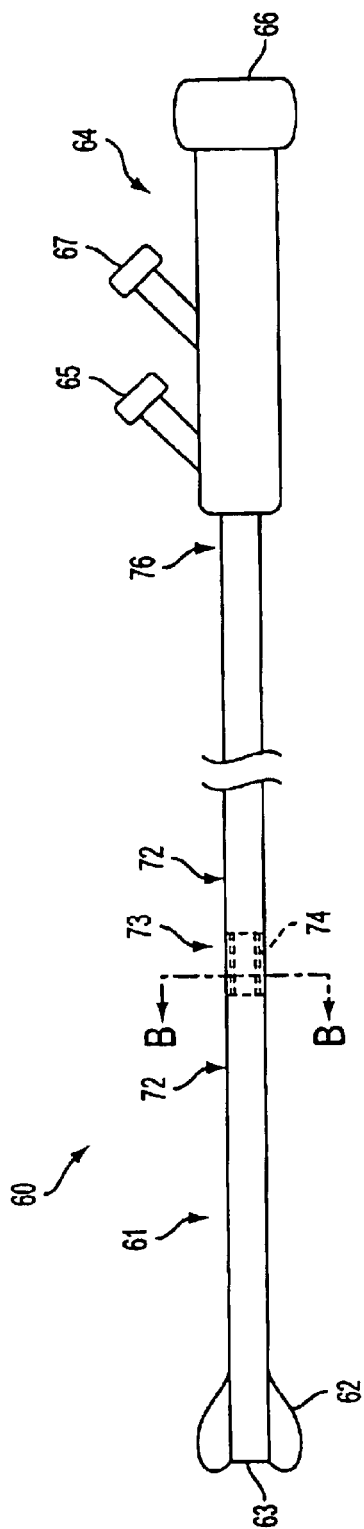
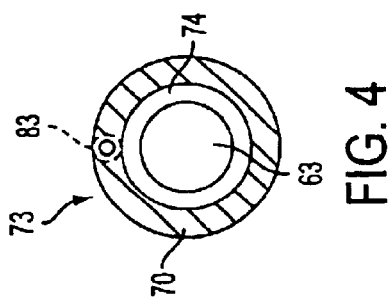
FIG. 3
FIG. 4

CATHETER HAVING A COMPLIANT MEMBER CONFIGURED TO REGULATE ASPIRATION RATES

FIELD OF THE INVENTION

The present invention relates to apparatus and methods for regulating rates of aspiration during a medical procedure, and more specifically, a catheter that self-regulates aspiration rates through a working lumen of the catheter.

BACKGROUND OF THE INVENTION

Today there is a growing need to provide controlled access and vessel management during such procedures as stenting, atherectomy or angioplasty. Generally, during these procedures there is a high opportunity for the release of embolic material. The emboli may travel downstream from the occlusion, lodging deep within the vascular bed and causing ischemia. The resulting ischemia may pose a serious threat to the health or life of a patient if the blockage forms in a critical area, such as the heart, lungs, or brain.

Several previously known methods and apparatus incorporate the use of an external suction system in conjunction with an aspiration catheter for removal of clots, removal of embolic particles, or general flow management in a vessel. However, there are several risks associated with using an external suction system during such medical interventions.

For example, if the amount of suction is too high, trauma may be imposed upon the vessel, resulting in vessel dissections or spasms. Additionally, an excessively high rate of aspiration may facilitate clot formation within the vessel. Moreover, if an external suction pump is utilized, excessively high aspiration rates may result in excessive blood loss, requiring infusion of non-autologous blood and raising related safety issues.

Traditional methods for regulating aspiration rates used with suction pumps have relied on external pressure adjustments, e.g., requiring physician monitoring of the suction rates, which may lead to an incorrect amount of suction for a given set of circumstances and present risk of the above-mentioned complications. Previously-known safety mechanisms, such as relief valves, have been employed and typically are coupled to the proximal end of the catheter. However, such features may require additional parts or assembly to regulate flow.

In view of these drawbacks of previously known systems, it would be desirable to provide apparatus and methods for self-regulating aspiration rates through a working lumen of a catheter to reduce trauma imposed upon a patient's vessel.

It also would be desirable to provide apparatus and methods that regulate aspiration rates using a mechanism that is an inherent feature of the catheter, to eliminate the need for continuous aspiration monitoring with the potential for human error.

It further would be desirable to provide apparatus and methods that reduce the likelihood of kinking when the catheter comprises a compliant member configured to regulate flow.

It still further would be desirable to provide apparatus and methods for self-regulating aspiration rates that may be tailored for use in specific applications, e.g., cerebral and cardiovascular interventions.

SUMMARY OF THE INVENTION

In view of the foregoing, it is an object of the present invention to provide apparatus and methods for self-regulating aspiration rates through a working lumen of a catheter to reduce trauma imposed upon a patient's vessel.

It is also an object of the present invention to provide apparatus and methods that regulate aspiration rates using a mechanism that is an inherent feature of the catheter, to eliminate the need for continuous aspiration monitoring with the potential for human error.

It is a further object of the present invention to provide apparatus and methods that reduce the likelihood of kinking when the catheter comprises a compliant member configured to regulate flow.

It is yet another object of the present invention to provide apparatus and methods for self-regulating aspiration rates that may be tailored for use in specific applications, e.g., cerebral and cardiovascular interventions.

These and other objects of the present invention are accomplished by providing a catheter having proximal and distal ends and a working lumen extending therebetween. The catheter comprises a compliant member having an open position, whereby fluid flow through the working lumen is not substantially constrained, and a closed position whereby fluid flow through the working lumen is at least partially occluded. The compliant member is transformed from the open position to the closed position when a predetermined degree of suction is applied to the working lumen. In the closed position, the compliant member serves to occlude flow through the working lumen and mitigate the rate of aspiration imposed upon a patient's vessel.

In a preferred embodiment, a catheter provided in accordance with the present invention comprises a compliant section disposed between two relatively rigid sections. The compliant section comprises a polymer cover and the compliant member, which is in communication with the working lumen. The relatively rigid sections preferably comprise the polymer cover, a wire braid and an inner layer, which is in communication with the working lumen. The relatively rigid sections are less compliant than the compliant section due to the presence of the wire braid. An inner surface of the compliant member is substantially flush with an inner surface of the inner layer to facilitate a substantially undisturbed fluid flow through the working lumen.

The catheter of the present invention may be coupled to a suction-assisted aspiration device, e.g., a syringe, or may be used in conjunction with other aspiration techniques described hereinbelow. When the level of aspiration provided through the working lumen is at an acceptable rate, i.e., induced by a level of suction that will not impose significant trauma upon a patient's vessel, the compliant member remains in the open position and does not impede fluid flow through the working lumen.

When a predetermined aspiration threshold is exceeded, however, the rigidity of the compliant member is overcome, thereby causing the compliant member to transform to the closed position. The compliant member is temporarily drawn inward to at least partially occlude flow through the working lumen and impede aspiration from the patient's vessel. When the level of suction falls below the threshold level, the compliant member returns to the open position.

Advantageously, the self-regulating compliant member of the present invention is a feature that may be built directly into the catheter, thus alleviating the need to assemble additional components. Alternatively, the valve may be constructed as a separate add-in piece. Additionally, the catheter may be tailored for use for a particular application, e.g., cerebral and cardiovascular interventions, by varying the material properties or configuration of the compliant member, which in turn varies the aspiration threshold for which the compliant member is actuated.

Apparatus and methods also are disclosed to reduce the likelihood of kinking associated with the use of a compliant catheter section. During insertion of the catheter, a dilator preferably is used to enhance pushability of the catheter. Additionally, a reinforcement sheath may be employed to enclose the compliant section. In this embodiment, a proximal end of the reinforcement sheath is affixed to a first relatively rigid catheter section, and a distal end of the reinforcement sheath is affixed to a second relatively rigid catheter section. The compliant section is disposed between the first and section relatively rigid sections and is not affixed to the reinforcement sheath. This allows the compliant section to be drawn inward to occlude the working lumen, while enhancing structural integrity in the vicinity of the compliant section.

The compliant section preferably is disposed within a proximal region of the catheter, i.e., a region that is not introduced into a patient's body. This reduces the likelihood of kinking because the compliant section is not required to be advanced through a patient's tortuous vasculature. However, it will be apparent to one of skill in the art that the compliant member may be disposed at any region along the length of the catheter.

In an alternative embodiment of the present invention, the compliant member comprises a compliant sheath affixed to an inner layer of the catheter. The compliant sheath is affixed at first and second ends to the inner layer and remains in an open position, whereby the compliant sheath does not substantially impede flow through the working lumen, when an acceptable rate of aspiration is applied. When an aspiration threshold is exceeded, however, the compliant sheath is drawn inward to at least partially occlude flow through the working lumen and mitigate the rate of aspiration imposed upon a patient's vessel.

BRIEF DESCRIPTION OF THE DRAWINGS

Further features of the invention, its nature and various advantages will be more apparent from the accompanying drawings and the following detailed description of the preferred embodiments, in which:

FIG. 1 provides a side view of a previously-known catheter assembly;

FIG. 2 provides a cross-sectional view along line A—A of FIG. 1;

FIG. 3 provides a side view of a catheter assembly constructed in accordance with principles of the present invention;

FIG. 4 provides a cross-sectional view along line B—B of FIG. 3;

DETAILED DESCRIPTION OF THE INVENTION

Figure 5A:
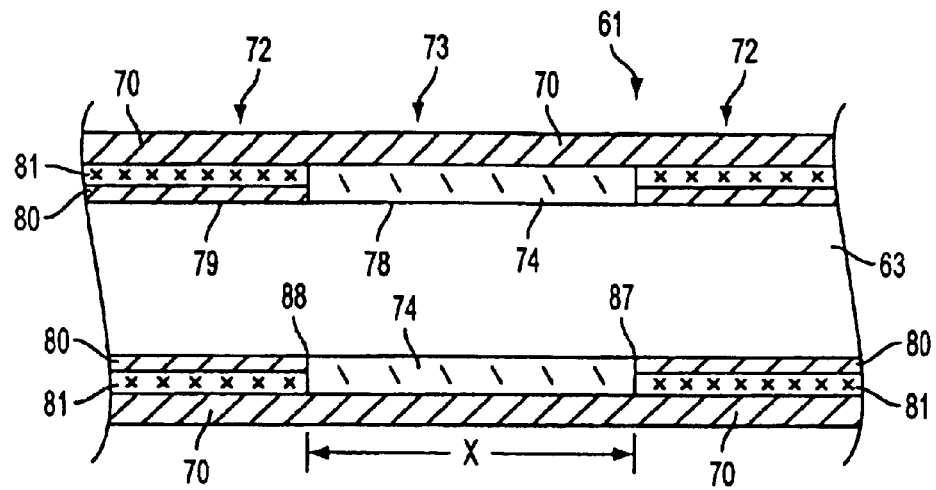
FIGS. 5A–5B are, respectively, side sectional views illustrating a compliant member of the present invention in open and closed positions.

The present invention is directed to a catheter that is configured to regulate aspiration rates through a working lumen of the catheter. The catheter comprises a compliant member in communication with the working lumen that transitions from an open position to a closed position when a predetermined level of aspiration is applied. In the closed position, the compliant member is drawn inward to at least partially occlude flow through the working lumen, thereby reducing the rate of aspiration provided through the working lumen and mitigating the rate of aspiration imposed upon a patient's vessel. When the rate of aspiration is reduced below the threshold level, the compliant member returns to the open position to reestablish an unimpeded flow through the working lumen.

Referring to FIG. 1, a previously known catheter assembly, described in applicant's commonly-assigned U.S. Pat. No. 6,423,032, is shown. Catheter assembly 20 comprises catheter 21 having proximal and distal ends and working lumen 23 extending therebetween. Catheter 21 also comprises occlusive element 22 disposed on the distal end, as shown in FIG. 1. Catheter 21 is coupled to proximal assembly 24, which may include inflation port 25, hemostatic port 26, e.g., a Touhy-Borst connector, and blood outlet port 27, each of which are in fluid communication with working lumen 23. Blood outlet port 27 may allow for either natural aspiration, using techniques described hereinbelow, or suction-assisted aspiration, e.g., using a syringe.

Referring to FIG. 2, a cross-sectional view along line A—A of FIG. 1 is provided. Catheter 21 preferably comprises inner layer 40 of low-friction material, such as polytetrafluoroethylene ("PTFE"), covered with a layer of flat stainless steel wire braid 41 and polymer cover 42 (e.g., polyurethane, polyethylene, or PEBAX). Inflation lumen 43 is disposed within polymer cover 42 and couples inflation port 25 to occlusive element 22. Catheter 41 may be configured for use in coronary, cerebral, or other vascular interventions.

In operation, catheter 21 preferably is advanced over a guidewire and dilator (not shown), using techniques that are per se known in the art. Catheter 21 is positioned in a selected vessel and occlusive element 22 is deployed via inflation port 25 to occlude antegrade flow in the vessel. Blood outlet port 27, which is in fluid communication with working lumen 23, may be coupled to an external aspiration device, e.g., a syringe, to cause blood flow distal of occlusive element 22 to flow in a retrograde fashion into working lumen 23. Alternatively, blood outlet port 27 may be coupled to a venous return sheath (not shown) to form an arterial-venous shunt suitable for providing retrograde flow in a treatment vessel. This aspiration embodiment comprising an arterial-venous shunt is described in detail in applicant's above-referenced patent.

As described hereinabove, the provision of suction-assisted aspiration through blood outlet port 27, e.g., to assist in the removal of emboli formed in a vessel during an interventional procedure performed through working lumen 23, poses significant risks to the vessel. First, it may be difficult to establish the proper aspirating pressure required at the treatment site, and external pressure adjustments used with suction pumps may lead to an incorrect amount of suction for a given set of circumstances. If the amount of suction is too high, the vessel may collapse or excessive blood loss may result. Accordingly, there is a need for a catheter having an inherent feature to prevent excessive rates of aspiration from being imposed upon a patient's vessel, particularly during the removal of emboli from the vessel.

Referring now to FIG. 3, apparatus constructed in accordance with a first embodiment of the present invention is described. Apparatus 60 preferably is provided substantially in accordance with apparatus 20 of FIG. 1, with the exception that catheter 61 having proximal and distal ends comprises compliant section 73 having compliant member 74. While compliant section 73 is illustratively depicted as being disposed in a central region of catheter 61, compliant section 73 may be disposed at the proximal or distal end of catheter 61, as described hereinbelow.

Referring to FIG. 4, a cross-sectional view along line B—B of FIG. 3 is provided. Compliant section 73 preferably comprises polymer cover 70 (e.g., polyurethane, polyethylene, or PEBAX) and compliant member 74. Inflation lumen 83 is disposed within polymer cover 70 and couples inflation port 65 to occlusive element 62. Compliant member 74 preferably is attached to an inner surface of polymer cover 70 and preferably comprises a tubular shape, as shown in FIG. 4. Working lumen 63, which is in fluid communication with blood outlet port 67 and hemostatic port 66 of FIG. 3, also is in communication with compliant member 74.

Referring now to FIG. 5, a side sectional view illustrating the inventive features of compliant section 73 are described. Compliant section 73 preferably is disposed between two relatively rigid catheter sections 72. Relatively rigid sections 72 preferably are provided in accordance with catheter 21 of FIGS. 1–2 and comprise inner layer 80 of low-friction material, such as polytetrafluoroethylene ("PTFE"), covered with a layer of flat stainless steel wire braid 81 and polymer cover 70, which preferably is the same cover that is affixed to an outer surface of compliant member 74, as shown in FIG. 5A. Inflation lumen 83 of FIG. 4 (which is not shown in FIG. 5A) is disposed within polymer cover 70 and spans the length of catheter 61.

Inner layer 80 and wire braid 81 preferably are disposed adjacent compliant member 74 at proximal and distal locations 87 and 88. Compliant section 73 is more compliant relative to sections 72 due to the absence of wire braid 81. Compliant member 74 preferably is sized to replace a void created by the absence of inner layer 80 and wire braid 81 between proximal and distal locations 87 and 88. An outer surface of compliant member 74 preferably is affixed to an inner surface of polymer cover 70, while inner surface 78 of compliant member 74 is substantially flush with inner surface 79 of inner layer 80, as shown in FIG. 5A. This provides a substantially seamless transition between sections 72 and 73 to facilitate flow through working lumen 63.

In accordance with principles of the present invention, compliant member 74 comprises a material having properties that are more compliant than the combination of inner layer 80 and wire braid 81. This allows compliant section 73, which includes polymer cover 70 and compliant member 74, to be more compliant overall than section 72, which includes having polymer cover 70, wire braid 81 and inner layer 80.

During operation, aspiration may be provided through working lumen 63, and blood and/or emboli may be aspirated through working lumen 63 via blood outlet port 67 of FIG. 3, as described hereinabove. Also, an interventional procedure, such as balloon angioplasty or stenting, may be performed through working lumen 63 and hemostatic port 66 of FIG. 3.

When the rate of aspiration provided through working lumen 63 via blood outlet port 67 is appropriate, i.e., at such a rate that the aspiration generally will not cause damage to a patient's vessel, then compliant member 74 remains in an open position, as shown in FIG. 5A. This is because the aspiration force provided through the working lumen is not yet sufficient to overcome the resistance force inherent to compliant member 74. In the open position, fluid flow through working lumen 63 is not substantially constrained, as shown in FIG. 5A.

Figure 5B:
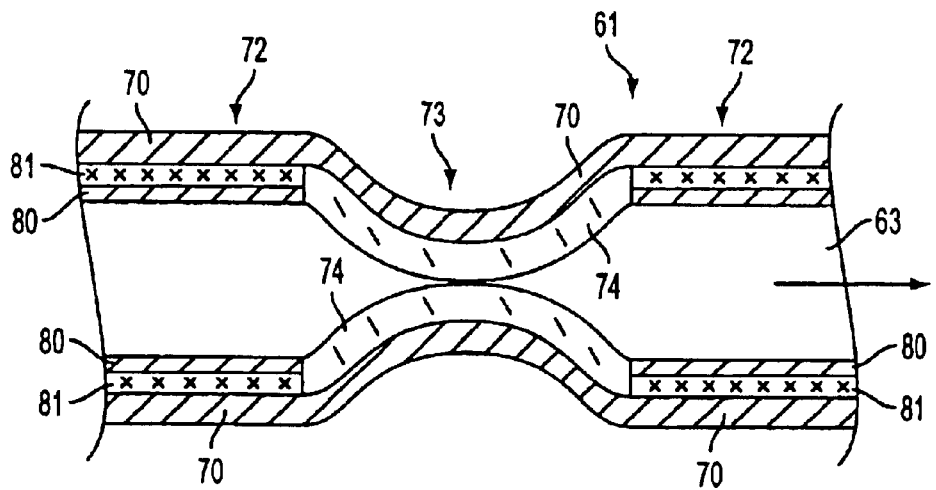

However, when the aspiration provided through working lumen 63 is increased above a predetermined threshold, i.e., at a rate so high as to generally cause damage to a patient's vessel (distal of occlusive member 62), then compliant member 74 is transformed from the open position of FIG. 5A to a closed position, as shown in FIG. 5B. Compliant member 74 is automatically drawn inward when the aspiration rate provided through working lumen 63 is sufficient to overcome the resistance force provided by compliant member 74. In the closed position, compliant member 74 is drawn inward to at least partially occlude flow through working lumen 63. Compliant member 74 may fully occlude working lumen 63 when the aspiration threshold is exceeded, as depicted in FIG. 5B, or alternatively may partially occlude working lumen 63 an amount proportional to the excessive rate of aspiration.

By causing compliant member 74 of compliant section 73 to at least partially occlude flow through working lumen 63, the rate of aspiration provided through working lumen 63 is reduced. This serves to mitigate the rate of aspiration imposed upon a patient's vessel and may reduce the risk of damage to the vessel that may be caused by an excessive rate of aspiration. When the level of aspiration applied through working lumen 63 falls below the threshold, then compliant member 74 returns to the open position shown in FIG. 5A to reestablish regular flow through working lumen 63.

In accordance with principles of the present invention, catheter 61 of the present invention reduces the likelihood of damage to a vessel from applying too much aspiration by automatically mitigating the rate of aspiration when it exceeds a predetermined threshold. Advantageously, this self-regulating mechanism may be provided as a built-in feature of the catheter, and thus eliminates the need for continuous aspiration monitoring with the potential and the attendant risk of human error.

As will be appreciated by those skilled in the art, the aspiration threshold for which compliant member 74 is drawn inward to occlude working lumen 63 may be determined by varying the characteristics of compliant member 74. For example, when compliant member 74 is manufactured of a more rigid material, then a higher rate of aspiration may be required to draw compliant member 74 into the working lumen. When compliant member 74 is manufactured of a less rigid material, a lower rate of aspiration is required to transform compliant member 74 between the open position of FIG. 5A and the closed position of FIG. 5B.

Additionally, the aspiration threshold for which compliant member 74 is drawn into working lumen 63 may be varied by varying longitudinal length x of compliant member 74. When length x is greater, a lower rate of aspiration may be required to draw compliant member 74 into working lumen 63 relative to the rate required when length x is smaller.

The aspiration threshold for which compliant member 74 is drawn into working lumen 63 may be predefined for specific medical interventions. For example, when catheter 61 is intended for use in conjunction with cerebral interventions, the predefined aspiration threshold may be relatively low to cause compliant member to mitigate aspiration rates as they become moderate or high, whereas a different threshold may be desired during cardiovascular interventions.

Although compliant section 73 is illustratively disposed in a central region of catheter 61 in FIG. 3, it may be preferable to dispose compliant section 73 within proximal region 76 (shown in FIG. 3), i.e., a proximal catheter region that is not introduced into a patient's vasculature. By disposing compliant section 73 in a proximal region that remains outside of a patient's body, the likelihood of kinking may be reduced because the compliant section is not advanced through a patient's tortuous vasculature. It should be noted that, even when compliant section 73 is disposed in a central or distal region, kinking is not expected to occur when a dilator (not shown) is used in conjunction with catheter 61 during insertion of the catheter.

Figure 6A:
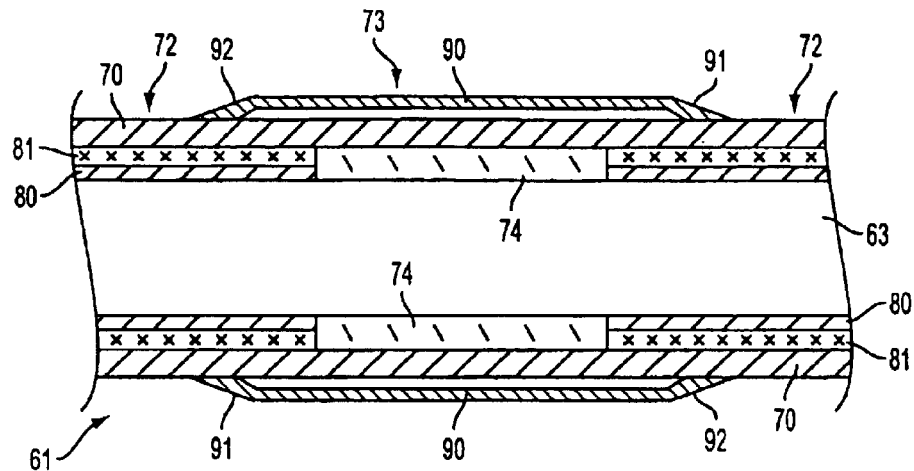
FIGS. 6A–6B illustrate the device of FIG. 5 further comprising a reinforcement sheath to enhance structural integrity.

Referring now to FIG. 6, reinforcement sheath 90 having proximal and distal ends 91 and 92 may be used in conjunction with compliant section 73 of the embodiment of FIG. 5 to further reduce the likelihood of kinking in the vicinity of compliant section 74. As shown in FIG. 6A, proximal end 91 of reinforcement sheath 90 is affixed to a first relatively rigid section 72 and distal end 92 is affixed to a second relatively rigid section 72. Reinforcement sheath 90 comprises a material that is more rigid than the combination of polymer cover 70 and compliant member 74, to help reduce kinking in the vicinity of compliant section 73.

Figure 6B:
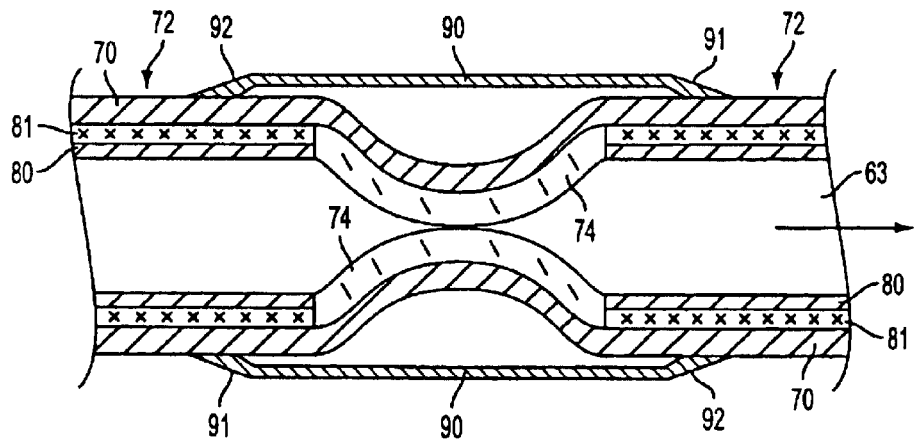

A central region of reinforcement sheath 90 encloses compliant section 73 but is not affixed to section 73, to allow compliant member 74 to be drawn into working lumen 63 when an aspiration threshold is exceeded, as shown in FIG. 6B. A diameter of the central region of reinforcement sheath 90 preferably is sized to be slightly larger than an outer diameter of catheter 61. Proximal and distal ends 91 and 92 further preferably comprises proximal and distal tapers, as depicted, to facilitate insertion of catheter 61.

Figure 7A:
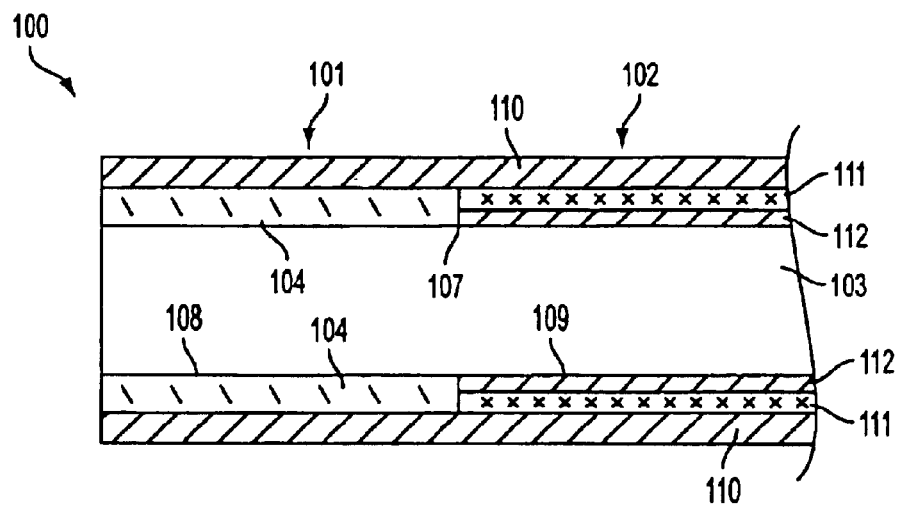
FIGS. 7A–7B are, respectively, side sectional views illustrating a compliant member of the present invention, which is disposed at the distal end of a catheter, in open and closed positions.

Referring now to FIG. 7, catheter 100 preferably is provided in accordance with catheter 61 of FIGS. 3–5, with the exceptions that compliant section 101 having compliant member 104 is disposed at the distal end of catheter 100 and occlusive element 62 is omitted. Compliant section 101 having compliant member 104 and polymer cover 110 is disposed distal of relatively rigid section 102 having inner layer 112, wire braid 111 and polymer cover 110. As described with respect to the embodiment of FIGS. 3–5, an outer surface of compliant member 104 preferably is affixed to polymer cover 110, while a first end of compliant member 104 is affixed to inner layer 112 and/or wire braid 111 of relatively rigid section 102 at location 107. Inner surface 108 of compliant member 104 preferably is substantially flush with inner surface 109 of inner layer 112 when compliant member 104 is in an open position, as shown in FIG. 7A.

Figure 7B:
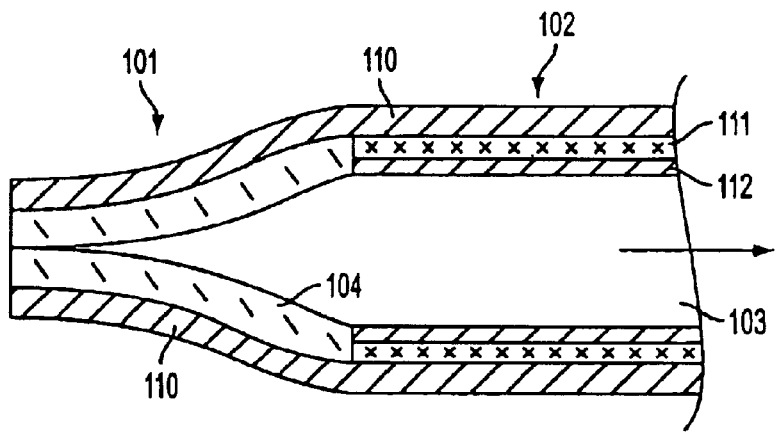

The distal end of catheter 100 is advanced over a dilator (not shown), which reduces the likelihood of kinking in the vicinity of distal section 101 during insertion of the device. Once the distal end of catheter 100 is positioned at the desired location, the dilator is removed from within working lumen 103 and aspiration may be provided through the working lumen. As described hereinabove, when the rate of aspiration exceeds a predetermined threshold, the rigidity of compliant member 104 is overcome and causes compliant member 104 to be drawn inward towards working lumen 103, as shown in FIG. 7B. Fluid flow through working lumen 103 is at least partially occluded to mitigate the rate of aspiration imposed upon a patient's vessel. When the rate of aspiration falls below the threshold to an acceptable rate, compliant member 104 returns to the open position shown in FIG. 7A to restore flow through working lumen 103.

Referring now to FIG. 8, an alternative embodiment of the present invention is described. Catheter 130 having proximal and distal ends and lumen 133 extending therebetween may be coupled to proximal assembly 24 of FIG. 1, which may include an inflation port, hemostatic port and blood outlet port, as described hereinabove. Unlike previous inventive embodiments, catheter 130 is constructed of a uniform material along its longitudinal length, as described with respect to the embodiment of FIGS. 1–2. Specifically, catheter 130 comprises polymer cover 140, wire braid 141, and inner layer 142 along its entire length, each of which may be constructed using materials described hereinabove.

Figure 8A:
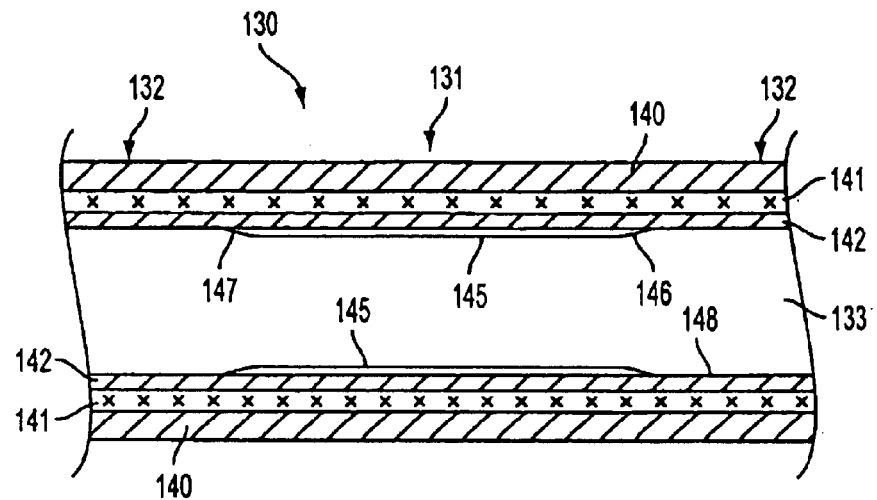
FIGS. 8A–8B describe an alternative embodiment of the present invention having a compliant sheath affixed to an inner layer of a catheter.

Catheter 130 additionally comprises compliant member 145, which includes a compliant sheath disposed within working lumen 133 and affixed to inner surface 148 of inner layer 142 at proximal and distal points 146 and 147, respectively. A central region of compliant sheath 145 is not affixed to inner layer 142. When an acceptable rate of aspiration is provided through working lumen 133, compliant sheath 145 is substantially rigid to hold compliant sheath 145 in an open position, as shown in FIG. 8A. In the open position, compliant sheath 145 does not substantially impede fluid flow through working lumen 133.

Figure 8B:
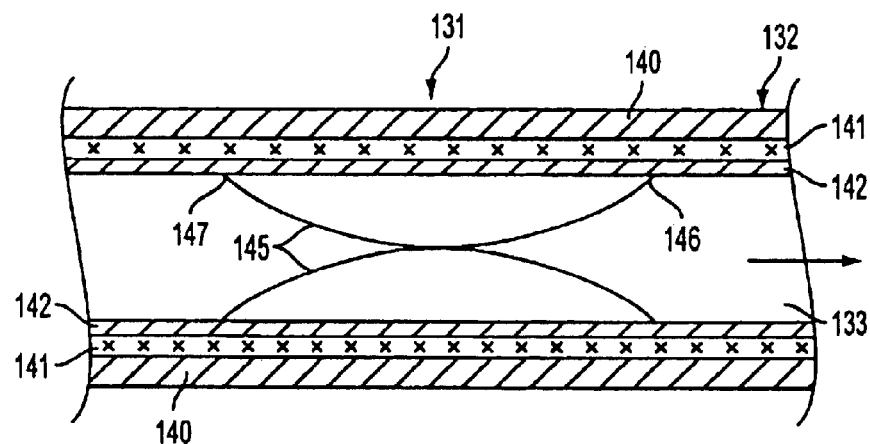

When a predetermined level of aspiration is exceeded, the rigidity of compliant sheath 145 is overcome, thereby causing sheath 145 to be drawn inward towards working lumen 133, as shown in FIG. 8B. Fluid flow through working lumen 133 is at least partially occluded to mitigate the rate of aspiration imposed upon a patient's vessel. When the rate of aspiration falls below the threshold to an acceptable rate, compliant sheath 145 returns to the open position shown in FIG. 8A to restore flow through working lumen 133.

Advantageously, the embodiment described in FIG. 8 comprises a uniform catheter body along its length and reduces the likelihood of kinking. It will be apparent to those skilled in the art that, like compliant member 74 of FIGS. 3–5, compliant sheath 145 of FIG. 8 may be tailored to deploy for a predetermined rate of aspiration, e.g., by varying the material properties or by varying the distance between proximal and distal points 146 and 147.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. Apparatus suitable for regulating the rate of aspiration provided through a working lumen of a catheter, the apparatus comprising:

a catheter having proximal and distal ends and a working lumen extending therebetween; and a compliant member coupled to the catheter in communication with the working lumen, the compliant member configured to transition from an open position when a level of aspiration through the working lumen is below a threshold value, and a closed position wherein the compliant member at least partially occludes flow through the working lumen when the level of aspiration exceeds the threshold value, wherein the compliant member is disposed within a compliant section comprising the compliant member and a polymer cover, the catheter further comprising at least one relatively rigid section disposed adjacent the compliant section.

2. The apparatus of claim 1 wherein the relatively rigid section comprises an inner layer, a wire braid, and the polymer cover.

3. The apparatus of claim 2 wherein an inner surface of the compliant member is substantially flush with an inner surface of the inner layer.

4. The apparatus of claim 1 wherein the compliant member is disposed within a proximal region of the catheter.

5. The apparatus of claim 1 wherein the compliant member is disposed at the distal end of the catheter.

6. The apparatus of claim 1 further comprising an inflation lumen disposed within the polymer cover, wherein the inflation lumen is coupled between an occlusive element disposed at the distal end of the catheter and an inflation port in communication with the proximal end of the catheter.

7. The apparatus of claim 1 further comprising a reinforcement sheath having proximal and distal ends, the reinforcement sheath disposed to enclose the compliant section.

8. The apparatus of claim 7 wherein the proximal end of the reinforcement sheath is affixed to the relatively rigid section of the catheter and the distal end of the reinforcement sheath is affixed to a second relatively rigid section of the catheter.

9. The apparatus of claim 8 wherein the proximal and distal ends of the reinforcement sheath are tapered.

10. The apparatus of claim 1 wherein the compliant section comprises a compliant sheath affixed to an inner layer of the catheter.

11. The apparatus of claim 1 wherein the compliant member is provided with a predetermined rigidity that is proportional to a predetermined aspiration threshold.

12. Apparatus suitable for regulating the rate of aspiration provided through a working lumen of a catheter, the apparatus comprising:
   a catheter having proximal and distal ends and a working lumen extending therebetween; and
   a compliant member coupled to the catheter in communication with the working lumen, the compliant member configured to transition from an open position when a level of aspiration through the working lumen is below a threshold value, and a closed position wherein the compliant member at least partially occludes flow through the working lumen when the level of aspiration exceeds the threshold value,
   wherein the compliant member is disposed within a compliant section located at the distal end of the catheter, the compliant section comprising the compliant member and a polymer cover.

13. The apparatus of claim 12 wherein the catheter further comprises at least one relatively rigid section disposed adjacent the compliant section.

14. The apparatus of claim 13 wherein the relatively rigid section comprises an inner layer, a wire braid, and the polymer cover.

15. The apparatus of claim 14 wherein an inner surface of the compliant member is substantially flush with an inner surface of the inner layer.

16. The apparatus of claim 12 further comprising an inflation lumen disposed within the polymer cover, wherein the inflation lumen is coupled between an occlusive element disposed at the distal end of the catheter and an inflation port in communication with the proximal end of the catheter.

17. The apparatus of claim 12 wherein the compliant section comprises a compliant sheath affixed to an inner layer of the catheter.

18. The apparatus of claim 12 wherein the compliant member is provided with a predetermined rigidity that is proportional to a predetermined aspiration threshold.

19. Apparatus suitable for regulating the rate of aspiration provided through a working lumen of a catheter, the apparatus comprising:
   a catheter having proximal and distal ends and a working lumen extending therebetween; and
   a compliant member coupled to the catheter in communication with the working lumen, the compliant member configured to transition from an open position when a level of aspiration through the working lumen is below a threshold value, and a closed position wherein the compliant member at least partially occludes flow through the working lumen when the level of aspiration exceeds the threshold value,
   wherein the compliant member comprises a compliant sheath affixed to an inner layer of the catheter.

20. The apparatus of claim 19 wherein the compliant member is disposed within a compliant section, the compliant section comprising the compliant sheath and a polymer cover.

21. The apparatus of claim 20 wherein the catheter further comprises at least one relatively rigid section interposed between the compliant sheath and the polymer cover.

22. The apparatus of claim 21 wherein the relatively rigid section comprises a wire braid.

23. The apparatus of claim 22 wherein an inner surface of the compliant member is substantially flush with an inner surface of the inner layer.

24. The apparatus of claim 19 wherein the compliant member is disposed within a proximal region of the catheter.

25. The apparatus of claim 19 wherein the compliant member is disposed at the distal end of the catheter.

26. The apparatus of claim 20 further comprising an inflation lumen disposed within the polymer cover, wherein the inflation lumen is coupled between an occlusive element disposed at the distal end of the catheter and an inflation port in communication with the proximal end of the catheter.

27. The apparatus of claim 20 further comprising a reinforcement sheath having proximal and distal ends, the reinforcement sheath disposed to enclose the compliant section.

28. The apparatus of claim 27 wherein the proximal end of the reinforcement sheath is affixed to a first relatively rigid section of the catheter and the distal end of the reinforcement sheath is affixed to a second relatively rigid section of the catheter.

29. The apparatus of claim 28 wherein the proximal and distal ends of the reinforcement sheath are tapered.

30. The apparatus of claim 19 wherein the compliant member is provided with a predetermined rigidity that is proportional to a predetermined aspiration threshold.

* * * * *